United States Patent [19]
Griswold

[11] Patent Number: 6,036,686
[45] Date of Patent: Mar. 14, 2000

[54] CRYOSURGICAL INSTRUMENT WITH GRIP

[75] Inventor: Thomas A. Griswold, Ellington, Conn.

[73] Assignee: Brymill Corporation, Vernon, Conn.

[21] Appl. No.: 09/135,207

[22] Filed: Aug. 17, 1998

[51] Int. Cl.[7] .................................................. A61B 17/36
[52] U.S. Cl. ................................ 606/20; 606/21; 606/22; 606/23; 606/25; 606/26; 220/560.04; 220/739
[58] Field of Search ................................. 606/20, 21, 22, 606/23, 24, 25, 26; 220/560.04, 560.12, 560.15, 701, 739, 740

[56] References Cited

U.S. PATENT DOCUMENTS

| | | | |
|---|---|---|---|
| 3,889,681 | 6/1975 | Waller et al. | 606/22 |
| 4,043,341 | 8/1977 | Tromovitch | 606/22 |
| 4,367,743 | 1/1983 | Gregory | 606/22 |
| 4,376,376 | 3/1983 | Gregory | 62/48.1 |
| 4,865,028 | 9/1989 | Swart | 606/23 |
| 5,098,428 | 3/1992 | Sandlin et al. | 606/22 |
| 5,658,276 | 8/1997 | Griswold | 606/24 |
| 5,738,682 | 4/1998 | Jensma | 606/23 |

*Primary Examiner*—Linda C. M. Dvorak
*Assistant Examiner*—Brad C. Blaise
*Attorney, Agent, or Firm*—M. P. Williams

[57] ABSTRACT

A hand-held cryosurgical instrument is provided with an insulating, cold-resistive, non-slip grip, which fits onto the neck of a cryosurgical instrument by means of machined threads. The grip has a lip for the users hand to rest against to protect it from the cold metal of the instrument.

4 Claims, 2 Drawing Sheets

CRYOSURGICAL INSTRUMENT WITH GRIP

TECHNICAL FIELD

This invention relates to cryosurgical instruments, and more particularly to a cold-resistive grip for cryosurgical instruments.

BACKGROUND ART

As seen in FIG. 1, the cryosurgical instrument most commonly used comprises a reservoir including a double metal wall vacuum bottle 10, modified for use with liquefied cryogen by provision of a collar 11 at the top thereof (shown only in FIG. 3) which encompasses the joint between the two metal walls, and by provision of a vent hole (not shown) in the bottom pan that protects the vacuum seal thereof. The collar 11 is provided with machined threads 12 (FIG. 3) to permit joining the vacuum bottle 10 to a cap 13 having threads 14 (FIG. 3) which mounts the control and delivery portion 15 of the instrument. The forerunner of the instrument of FIGS. 1 and 2 is set forth in U.S. Pat. No. 4,116,199. In recent years, the neck (upper outside portion) of the instrument has been fitted with a polyfoam collar 16 for an insulated grip, because the metal of the instrument becomes cold during use. However, the users hand may tend to slide and be forced to rest on the lip of the metal cap 13, which becomes very cold to the touch during use. To overcome this problem, a second foam collar 17 (FIG. 2) may be slipped over the upper part of the collar 16 and the cap 13; and a single large collar has been used instead of the two collars 16, 17.

However, the polyfoam collars that extend over the cap must be folded down (like a turtle neck sweater) or removed whenever the cap is removed for filling the instrument with cryogen. Furthermore, the collars cannot be sterilized in an autoclave, since the polyfoam will shrink into useless circlets. Therefore, devices using such collars cannot be used in a sterile theater, such as an operating room.

DISCLOSURE OF THE INVENTION

Objects of the invention include provision of an insulative, cold-resisting, non-slip grip for use with hand-held cryosurgical instruments which does not interfer with filling of the instrument and which may be autoclaved.

According to the present invention, an insulated, cold-resistive, non-slip grip for use with hand-held cryosurgical instruments is made of a hard, insulative plastic, such as DELRIN® or RADEL®, and has a lip which catches the users hand, keeping it from touching the metal cap of the instrument. The grip is provided with machined threads which engage complementary rolled threads on the neck of the cryosurgical instrument Other objects, features and advantages of the present invention will become more apparent in the light of the following detailed description of exemplary embodiments thereof, as illustrated in the accompanying drawing.

BEST MODE FOR CARRYING OUT THE INVENTION

Figure 1:
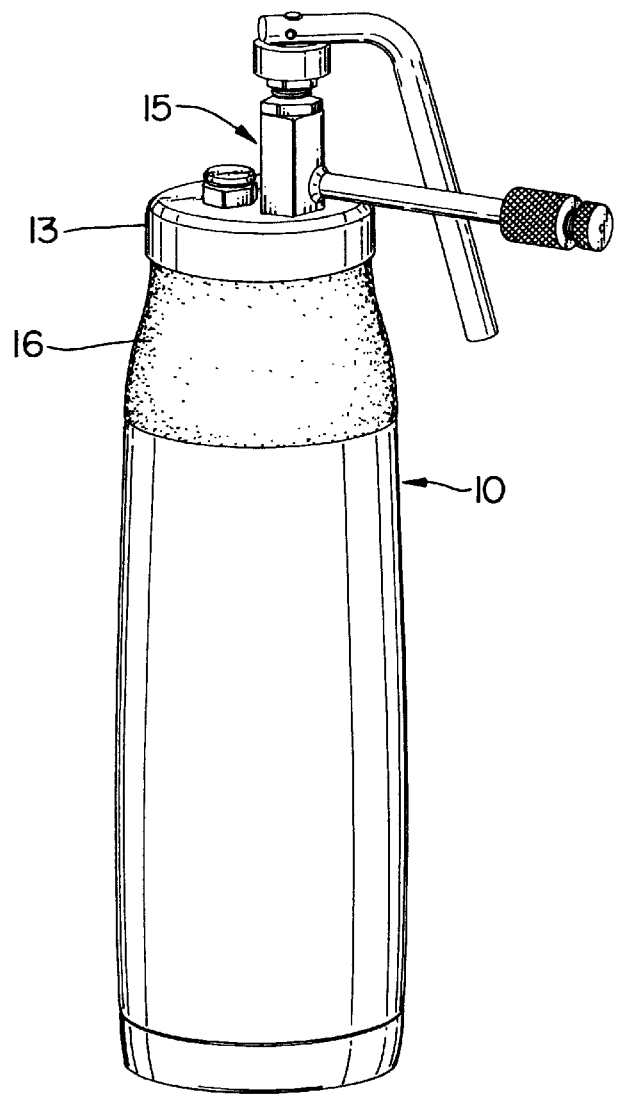
FIG. 1 is a perspective view of a first sample of a cryosurgical unit of the prior art.
Figure 2:
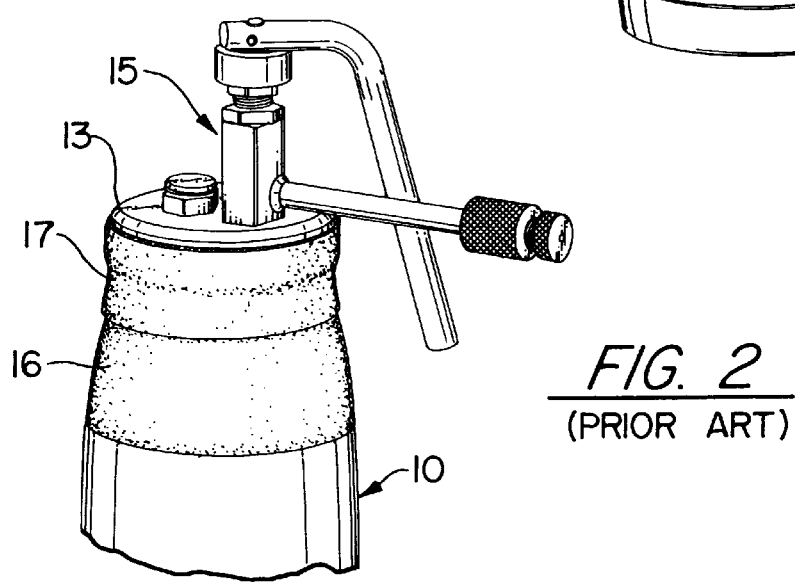
FIG. 2 is a partial perspective view of a second sample of a cryosurgical unit of the prior art
Figure 3:
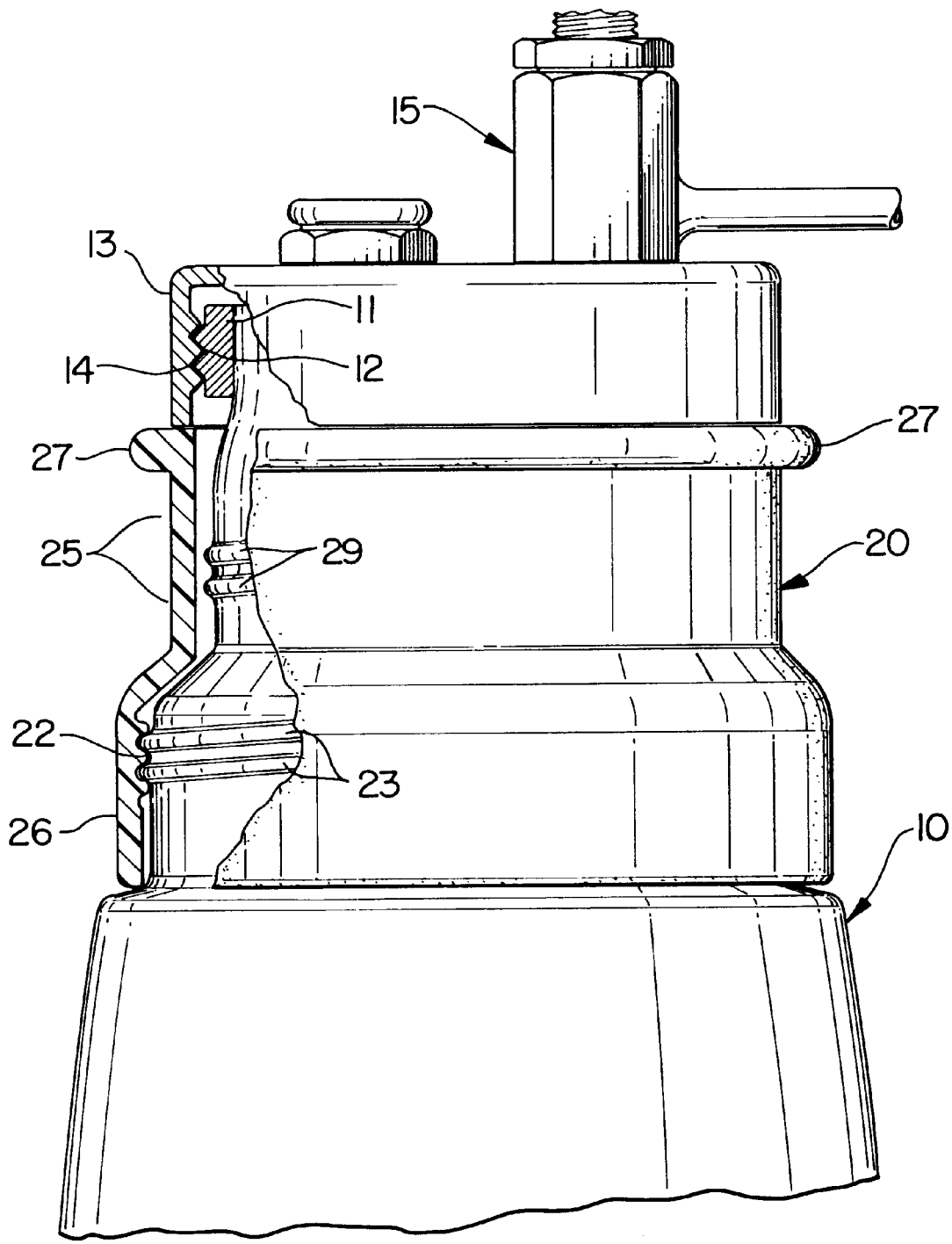
FIG. 3 is a partial, partially broken away and sectioned side elevation view of a preferred embodiment of the invention.

Referring now to FIG. 3, a generally cylindrical, insulating, cold-resistive, non-slip grip 20 according to the present invention is made of a hard plastic which is a poor conductor of heat, such as DELRIN and encompasses the neck of the cryosurgical instrument. If excessive autoclaving is required, the grip 20 may be made of RADEL.

The grip 20 fits onto the neck of the instrument by means of machined threads 22 which engage rolled threads 23 on the vacuum bottle 10 that normally secure a drinking cup on a conventional vacuum bottle. The grip is shaped to be indented in the middle, having an easily grasped, reduced diameter portion 25, between an enlarged diameter portion 26 at the bottom and a lip 27 at the upper edge, against which the users hand may rest. The lip 27 protrudes out from the cap 13, to keep the users hand from touching the cold metal of the cap. The vacuum bottle 10 may have a second set of rolled threads 29; the grip 20 may be formed to be secured by the threads 29 instead of or in addition to the threads 23. The grip may be subjected to innumerable autoclave cycles, and it does not interfere with filling the vacuum bottle 10.

The aforementioned patent is incorporated herein by reference.

Thus, although the invention has been shown and described with respect to exemplary embodiments thereof, it should be understood by those skilled in the art that the foregoing and various other changes, omissions, and additions may be made therein and thereto, without departing from the spirit and scope of the invention.

I claim:

1. A cryosurgical instrument, comprising:
   a reservoir for holding cryogen, said reservoir having a threaded collar joined to an upper edge thereof; and
   a threaded cap, including a cryogen delivery and control portion, secured to said collar through the engagement of the internal threads of the cap with the external threads of the collar;
   characterized by the improvement comprising:
   said reservoir having exterior threads near an upper end thereof below said collar, and
   a generally cylindrical grip composed of a hard, insulating plastic, said grip having internal threads complimentary to said external threads, said grip being joined to said reservoir by said exterior and interior threads.

2. A cryosurgical instrument according to claim 1 wherein:
   said grip has a peripheral lip extending outwardly of an upper edge thereof.

3. A cryosurgical instrument according to claim 2 wherein:
   said grip has a lower, increased diameter portion and a reduced diameter portion extending between said increased diameter portion and said lip.

4. A cryosurgical instrument having a hand-held grip, said grip being formed of rigid plastic and having a generally cylindrical shape with a reduced diameter portion near a first end, an enlarged diameter portion near a second end, having internal machined threads therein which are complementary to external rolled threads on a neck of said cryosurgical instrument, and a lip extending radially outward around the entire periphery of said reduced diameter portion at said first end.

* * * * *